(12) United States Patent
Savelkoul et al.

(10) Patent No.: US 8,536,321 B2
(45) Date of Patent: Sep. 17, 2013

(54) **COMPOSITIONS, METHODS, AND KITS FOR THE DETECTION OF *CHLAMYDIA TRACHOMATIS***

(75) Inventors: Paul Hendrik Maria Savelkoul, Amsterdam (NL); Arnold Catsburg, Amsterdam (NL); Antonie Servaas Morre, Amsterdam (NL)

(73) Assignee: Vereniging voor christelijk hoger onderwijs, wetenschappelijk onderzoek en patientenzorg, Amsterdam (NL)

( * ) Notice: Subject to any disclaimer, the term of this patent is extended or adjusted under 35 U.S.C. 154(b) by 489 days.

(21) Appl. No.: 12/525,998

(22) PCT Filed: Feb. 6, 2008

(86) PCT No.: PCT/NL2008/000036
§ 371 (c)(1),
(2), (4) Date: Oct. 6, 2010

(87) PCT Pub. No.: WO2008/097082
PCT Pub. Date: Aug. 14, 2008

(65) Prior Publication Data
US 2011/0020796 A1    Jan. 27, 2011

(30) Foreign Application Priority Data
Feb. 6, 2007   (NL) .................................. 1033345

(51) Int. Cl.
*C07H 21/04* (2006.01)
(52) U.S. Cl.
USPC ....... 536/24.33; 435/6.1; 435/6.11; 435/6.12; 536/1.11; 536/18.7; 536/22.1; 536/23.1; 536/24.3

(58) Field of Classification Search
None
See application file for complete search history.

(56) References Cited

FOREIGN PATENT DOCUMENTS

| | | |
|---|---|---|
| EP | 0 915 170 | 5/1999 |
| EP | 0 915 173 | 5/1999 |
| EP | 1 598 431 | 11/2005 |
| EP | 1 602 734 | 12/2005 |
| WO | WO-01/40474 | 6/2001 |

OTHER PUBLICATIONS

Bauwens et al., "Diagnosis of *Chlamydia trachomatis* endocervical infections by a commercial polymerase chain reaction assay," Journal of Clinical Microbiology, 1993, vol. 31, No. 11, pp. 3023-3027.*
GenBank Accession No. X07547, publicly avaialble Feb. 1999 [retrieved on-line: www.ncbi.nlm.nih.gov/nuccore/X07547.*
New England BioLabs® catalog, 1998, pp. 1-3.*
International Search Report dated May 26, 2008 from PCT/NL2008/000036.

\* cited by examiner

*Primary Examiner* — Young J Kim
(74) *Attorney, Agent, or Firm* — Foley Hoag LLP

(57) ABSTRACT

Method for the detection of *Chlamydia trachomatis*, which method comprises the performance of a DNA amplification involving the use of a primer pair by using DNA that is derived from a sample as a template and the detection of an amplification product, characterized in that the primer pair used for the DNA amplification is designed on the basis of nucleotide sequences of the regions corresponding to the nucleotide numbers 3654 to 4320 and 4351 to 4448 in the nucleotide sequence of SEQ ID No. 1.

Figure 1:
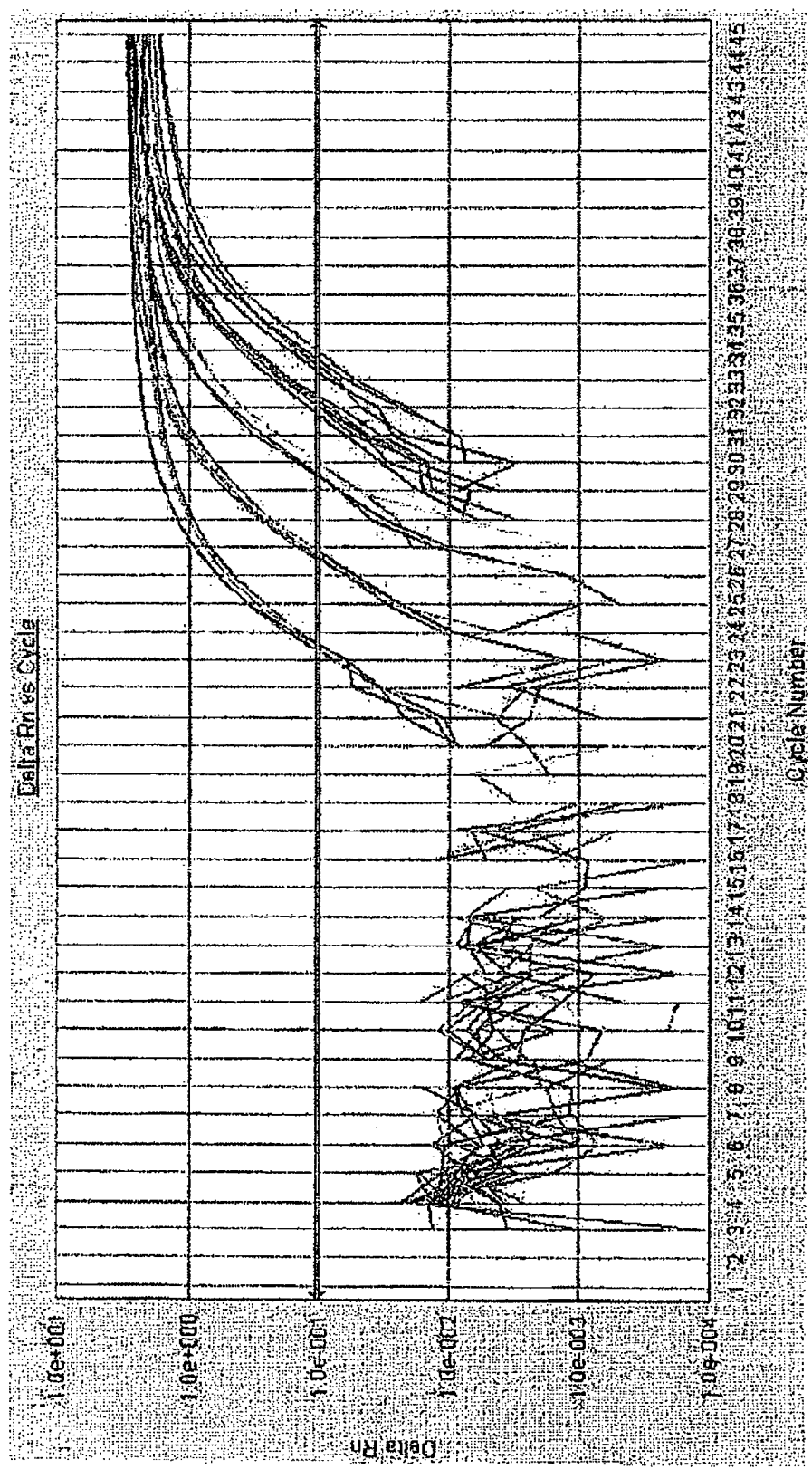

18 Claims, 2 Drawing Sheets

COMPOSITIONS, METHODS, AND KITS FOR THE DETECTION OF *CHLAMYDIA TRACHOMATIS*

RELATED APPLICATIONS

This application is the U.S. National Stage Application of International Application No. PCT/NL2008/000036, filed on Feb. 6, 2008, which claims the benefit of priority to the Netherlands Patent Application No. 1033345, filed on Feb. 6, 2007; the contents of each of which application is incorporated herein in its entirety by this reference.

The present invention relates to a method for the detection of *Chlamydia trachomatis* and to a kit for it.

*Chlamydia trachomatis* is one of the non-gonococcal urethritis pathogens that contains a cryptic plasmid [M. Commanducci et al., *Mol. Microbiol.*, 2, No. 4 (1998), pp. 531-538]. A method for detecting *Chlamydia trachomatis*, a method for amplifying a partial sequence of the cryptic plasmid by a gene amplification process is known (JP 2719225 and JP 3127135).

It has been found that problems arise with the observation and/or detection of *Chlamydia trachomatis* under certain conditions. An article by Söderblom et al. (*Euro Surveill* 2006 Dec. 7; 11 (12)): E061207.1) entitled "Impact of a genetic variant of *Chlamydia trachomatis* on national detection rates in Sweden" reports that part of the sexually transmitted *Chlamydia trachomatis* infections could not be observed in Sweden by the standard laboratory tests produced by Abbott and Roche, and that *Chlamydia* bacteria with a variation in the genetic region to which the primers had been directed were not observed.

There is therefore a need for alternatives to the standard tests whereby for example such genetic variants of *Chlamydia trachomatis* can in fact be observed.

The goal of the present invention is therefore to provide a method for the rapid detection of *Chlamydia trachomatis*, which has a good sensitivity and specificity, and a kit for it.

The goal of the invention is achieved by a method for the detection of *Chlamydia trachomatis*, which method comprises the performance of a DNA amplification involving the use of a primer pair by employing DNA derived from a sample as a template, and the detection of an amplification product, characterized in that the primer pair employed for the DNA amplification is designed on the basis of nucleotide sequences of the regions corresponding to the nucleotide numbers 3654 to 4320 and 4351 to 4448 in the nucleotide sequence of SEQ ID No. 1 (i.e. they are in the ORF3 region of the above-mentioned cryptic plasmid, as is well known to the person skilled in the art).

The inventors have found that when a DNA amplification, such as for example PCR (whenever PCR is mentioned in the context of the present Application, the intended meaning is DNA amplification, of which PCR is an embodiment) is carried out with primers that are designed on the basis of such specific regions in the cryptic plasmid of *Chlamydia trachomatis*, *Chlamydia trachomatis* can be rapidly observed, and for example also the known *Chlamydia trachomatis* variants, such as those found for example in Sweden can also be observed. Another suitable method of DNA amplification for the determination of pathogens is described in WO 2005/060725 and is hereby incorporated by reference.

The primer pair for the DNA amplification, such as PCR, is preferably designed on the basis of nucleotide sequences of the regions corresponding to the nucleotide numbers 4261 to 4320 and 4351 to 4391, more preferably to the nucleotide numbers 4291 to 4320 and 4355-4385 and most preferably to the nucleotide numbers 4296 to 4318 and 4361 to 4382 of SEQ ID No. 1.

It has been found that the results improve as the preference increases for the nucleotide regions on the basis of which the separate primers for the primer pair are designed. In other words, the preference given above is based on the better results obtained with the primer pair in the preferred regions specified.

In other words, the primer pair with the greatest preference is designed on the basis of nucleotide sequences of the regions in SEQ ID No. 1: GGATT GACTCCGACA ACGTATTC (SEQ ID NO: 2.) and TGCCCTTTCT AATGGCAATGAT (SEQ ID NO: 3), corresponding respectively to the region of 4296 to 4318 and of 4361 and 4382 in SEQ ID No. 1. A first primer is preferably directed to the whole region GGATT GACTCCGACA ACGTATTC (SEQ ID NO: 2), and the second primer of the primer pair is directed to the whole region TGCCCTTTCT AATGGCAATGAT (SEQ ID NO: 3). The person skilled in the art will understand that the other regions described above can be established on the basis of what has been said above.

The person skilled in the art will understand that DNA derived from a sample means DNA that is isolated or is obtained from an organism, such as a person, to be tested, but it also covers copies, replicates and processed forms of such DNA, obtained for example by chemical synthesis or PCR, starting with the original DNA isolated from the organism.

The sample used is not particularly subject to restrictions, provided that it contains or can contain *Chlamydia trachomatis*. Examples of this comprise urine, urethral (urinary tube) scrapings, cervical smears etc. DNA can be extracted from these samples by the method known to the person skilled in the art, whereby DNA, including DNA of the cryptic plasmid of *Chlamydia trachomatis*, can be prepared. It is particularly preferable to employ the Roche COBAS CT DNA preparation kit, because it has been found to give particularly advantageous results. It will be obvious to the person skilled in the art that the DNA can be either isolated pure DNA or DNA that is present in an unprocessed lysate.

The primer pairs that can be employed in the invention can therefore be chosen in the regions described above and in particular in such a way that the nucleotide region can be amplified/replicated between the two regions.

The primer pair used in the present invention is designed on the basis of a nucleotide sequence of the region corresponding to the nucleotide numbers 3654 to 4320, preferably 4261 to 4320, more preferably 4291 to 4320 and most preferably 4296 to 4318 (first region) and 4351 to 4448, preferably 4351 to 4391, more preferably 4355-4385 and most preferably 4361 to 4382 (second region), as mentioned above and in SEQ ID No. 1, so that the nucleotide sequence can be amplified (replicated) between these two regions with the aid of the primer pair.

According to the invention, the length of the primers is for example between 10 and 40 nucleotides. Furthermore, the position of each region and the length of the primers are preferably chosen so that the Tm value of the primer in question and the corresponding template DNA lies between 50 and 70° C., and so the annealing temperature used in the PCR can be set at a relatively high value. The Tm value used here is a value that is calculated by the nearest neighbour base pair analysis. The primers can basically have the same Tm value.

The person skilled in the art will understand that the term "designed on the basis of" means that, with the stipulations specified for the primer, such as the Tm value and the length of the primer, which are described herein, the primer is designed as such that it can be complementary to the sequence in either the sense strand or the antisense strand of the nucleotide sequence of the regions according to the invention described above and especially in the claims. The design therefore starts with the sequence on which the primer has to bind, and with the stipulations and in the context of the present invention, the primer can be complementary to the sequence on which it has to bind.

PCR is the method of detection according to the present invention, and it can be carried out in accordance with the normal PCR method, provided that the DNA obtained from the sample is used as a template, and that a specific primer set according to the invention is used. In particular, real-time PCR is employed in the method according to the invention (TaqMan assay, see the Example), because this has given particularly good results.

The primer pair can be designed in such a way that the nucleotide sequence between the two regions (i.e. the region between the location where a first primer will bind under the PCR conditions and the location where a second primer will bind under the PCR conditions) can be replicated (amplification). This means that one primer can be a sense primer, and the other can be an anti-sense primer.

The nucleotide sequence reproduced in SEQ ID No. 1 is derived from the cryptic plasmid of Chlamydia trachomatis (L2 strain), deposited with the GeneBank under access number X07547, based on Commanducci's publication (see above), and reproduced in Dutch Patent Application No. 103345, which is the priority document for the present Application and which is included here by reference. The person skilled in the art will understand that a PCR carried out with a primer pair according to the invention will be able to lead to the replication of the DNA in this cyclic plasmid. Since the cryptic plasmid is a cyclic plasmid, it has two nucleotide sequences between the two regions on the basis of which the primer pair is designed. However, the primers are usually so designed that the shorter nucleotide sequence can be replicated (amplification).

The examples of the preferred primer pairs according to the present invention comprise a combination of primer pairs that are designed on the basis of a nucleotide sequence of a region corresponding to the nucleotide numbers 3654 to 4320, preferably 4261 to 4320, more preferably 4291 to 4320 and most preferably 4296 to 4318 (first region) and on the basis of a nucleotide sequence of a region corresponding to the nucleotide numbers 4355-4385 and preferably 4361 to 4382 (second region).

Another preferred example of the primer pairs according to the present invention involves a combination of primer pairs designed on the basis of a nucleotide sequence of a region corresponding to the nucleotide numbers 4291 to 4320, preferably 4296 to 4318 (first region) and a nucleotide sequence of a region corresponding to the nucleotide numbers 4351 to 4448, preferably 4351 to 4391, more preferably 4355 to 4385 and most preferably 4361 to 4382 (second region).

Designing the nucleotide sequence of the primer pair is obvious to the person skilled in the art if he knows the corresponding sequences in SEQ ID No. 1, disclosed in this invention. SEQ ID No. 1 is one of the DNA strands of the double-stranded cryptic plasmid. This strand is called here the sense strand. The opposite strand, which is complementary to this sense strand, is called here the anti-sense strand. As for the amplification with the aid of for example PCR, the person skilled in the art will know that he should base the sequence of the primer of the primer pair to be used on the sequence described above, which corresponds to the sequence of the sense strand of the cryptic plasmid (the so-called "forward" primer). He will base the sequence of the other primer of the primer pair on the sequence of the anti-sense strand, called the "reverse" primer.

The sequences of the primers in question are preferably so chosen that the completed amplification leads to an amplification product that is specific to the envisaged cryptic plasmid's sequence to be amplified. The sequence of the selected primers therefore need not necessarily be completely identical to the said sequence in SEQ ID No. 1 described above (nor does it need not be fully complementary to it). Mismatches are admissible, provided that the specificity of the amplification is retained. By preference, the sequence of the primers agrees completely with the one defined by SEQ ID No. 1 (or with the sequence that is complementary to it).

In those cases occurring in practice where the specificity is relevant, for example when polymorphism can be expected in the DNA to be amplified, especially on sites in the DNA where one of the primers to be used should hybridize, it is preferable to use more than one primer whose sequence is complementary to the various polymorphisms. In such a primer set given below, there are two forward primers (which differ from each other only in one site of the sequence) and a single reverse primer. This makes it possible to detect a polymorphism in Chlamydia trachomatis G4307A in SEQ ID No. 1, which position is occupied by one of the primers to be used according to the invention. It is of course also possible in such a case to use a single forward primer and more than one reverse primer. If one wants to demonstrate a number of polymorphisms in a region where a primer hybridizes, one can employ the same number of different primers, each being specific to one such polymorphism.

The primer pair for the above-mentioned specific region can be designed with the aid of the methods that are known to the person skilled in the art, taking the PCR conditions into account. The primer pair can be designed by using a computer program.

The primer pair can be designed as a mixed primer obtained by mixing two or more primers for the sense or the anti-sense primer, or for both of them. When a nucleotide mutation occurs in the region for which the primer has been designed, the sensitivity of the observation/detection can be increased by using a mixed primer (see also below).

Although the PCR conditions can be determined in accordance with the customary PCR method, the annealing temperature can be set at a relatively high value, owing to the specific primer pairs mentioned here. The annealing temperature is usually between 50 and 70° C.

Another aspect of the invention relates to a kit for the detection of Chlamydia trachomatis by performing a PCR in which the DNA obtained from a sample is used as a template.

The kit that is particularly envisaged here for the detection of Chlamydia trachomatis by a PCR, using the DNA obtained from a sample as a template comprises a primer pair designed on the basis of nucleotide sequences of the regions corresponding to the nucleotide numbers 3654 to 4320 and 4351 to 4448 in the nucleotide sequence in SEQ ID No. 1.

More in particular, good results were obtained with a kit according to the invention that is characterized in that the primer pair is designed on the basis of nucleotide sequences of the regions corresponding to the nucleotide numbers 4261 to 4320 and 4351 to 4391; preferably to the nucleotide numbers 4291 to 4320 and 4355-4385, and most preferably to the nucleotide numbers 4296 to 4318 and 4361 to 4382 of SEQ ID No. 1.

Particularly favourable results are obtained with a kit that is characterized in that the primer pair in the kit is designed on the basis of nucleotide sequences of the regions in SEQ ID Nr.

1: GGATT GACTCCGACA ACGTATTC (SEQ ID No. 2) and TGCCCTTTCT AATGGCAATGAT (SEQ ID No. 3). As already explained above, the above sequences of the primers are all reproduced on the basis of the sense strand of the cryptic plasmid.

Another aspect of the invention relates to a primer pair designed on the basis of nucleotide sequences of the regions corresponding to the nucleotide numbers 3654 to 4320 and 4351 to 4448 in the nucleotide sequence of SEQ ID No. 1, in agreement with the goal of the invention, such as for example the detection of *Chlamydia trachomatis*. This means that the primer pairs envisaged according to the invention are those which are suitable for use for the detection of *Chlamydia trachomatis*.

More especially, the primer pairs according to the invention are characterized in that they are designed on the basis of the nucleotide sequences of the regions corresponding to the nucleotide numbers 4261 to 4320 and 4351 to 4391, preferably to the nucleotide numbers 4291 to 4320 and 4355-4385, and most preferably to the nucleotide number 4296 to 4318 and 4361 to 4382 of SEQ ID No. 1.

In the most preferred case, the primer pair is designed on the basis of nucleotide sequences of the regions in SEQ ID No. 1: GGATT GACTCCGACA ACGTATTC (SEQ ID No. 2) and TGCCCTTTCT AATGGCAATGAT (SEQ ID No. 3).

In a preferred embodiment, a primer pair with the following sequences is used:

```
                                        (SEQ ID NO: 2)
CT forward1 5'-GGA TTG ACT CCG ACA ACG TAT TC-3'

(SEQ ID NO: 6)
CT reverse  5'-ATC ATT GCC ATT AGA AAG GGC A-3'
```

As regards its sequence, CT forward corresponds to the nucleotides 4296-4318 of SEQ ID No. 1, and CT reverse corresponds to the anti-sense sequence of nucleotides 4361-4382 of SEQ ID No. 1.

In an advantageous embodiment of the invention, a primer set is also provided that comprises a primer pair according to the invention, together with a supplementary primer that differs in just one nucleotide from one of the primers of the primer pair as regards its sequence. As already explained above, this offers the possibility of demonstrating one or more polymorphisms in the regions in the cryptic plasmid with which one of the primers of the primer pair hybridizes.

It is even more preferable to add also a second forward primer to the primer pair in order to make it possible to detect G4307A polymorphism:

```
                                        (SEQ ID NO: 7)
CT forward2 5'-GGA TTG ACT CCA ACA ACG TAT TC-3'
```

Another aspect of the invention relates to a hybridization probe that can hybridize in the region replicated with the aid of the primer pair according to the invention. The hybridization probe preferably contains an oligonucleotide that is designed on the basis of the nucleotide sequence of the region corresponding to the nucleotide numbers 4320 to 4355, the hybridization probe being preferably designed on the basis of the nucleotide sequence TACGTGTAGG CGGTTTAGAA AGCGGGTGT (SEQ ID No. 4). In the most preferred case, the hybridization probe is aimed at the whole sequence described above and gives exceptionally good detection results. In particular, the hybridization probe has the following sequence:

```
CT reverse                              (SEQ ID NO: 8)
5'-ACA CCG CTT TCT AAA CCG CCT ACA CGT AA-3'
```

Such a hybridization probe is generally provided with a label for easy detection. The person skilled in the art knows the conditions under which hybridization is used; these conditions may be for example the same as those described in US 2006/0246447.

The person skilled in the art will understand that the hybridization probe used for the detection can be complementary either to a sense strand or to an anti-sense strand.

The chain length of the oligonucleotide is normally 15 to 30 nucleotides, and its Tm value can be 50 to 70° C.

When real-time PCR is used, the hybridization probe preferably has a Tm value that is 1 to 5 degC higher than the Tm value of a primer, so that the probe can hybridize with the target sequence before the primer is hybridized.

The invention is explained in more detail with the aid of the following examples and drawings, where:

FIG. 1 is a graph that shows the limit of detection of *Chlamydia trachomatis* and the internal reference (IR) sample in the real-time PCR test. The DNA used was derived from serial dilutions of *Chlamydia trachomatis* with 100, 10, 1, 0.1, e, 0.001 IFU/PCR. The slope of the graph is −2.9, the intercept is 29.4 and $R^2$ is 0.994. The x axis of the graph represents the initial IFU values of *Chlamydia trachomatis*, expressed as log IFU equivalents per PCR reaction. The y axis represents the threshold cycle ($C_T$).

Figure 2:
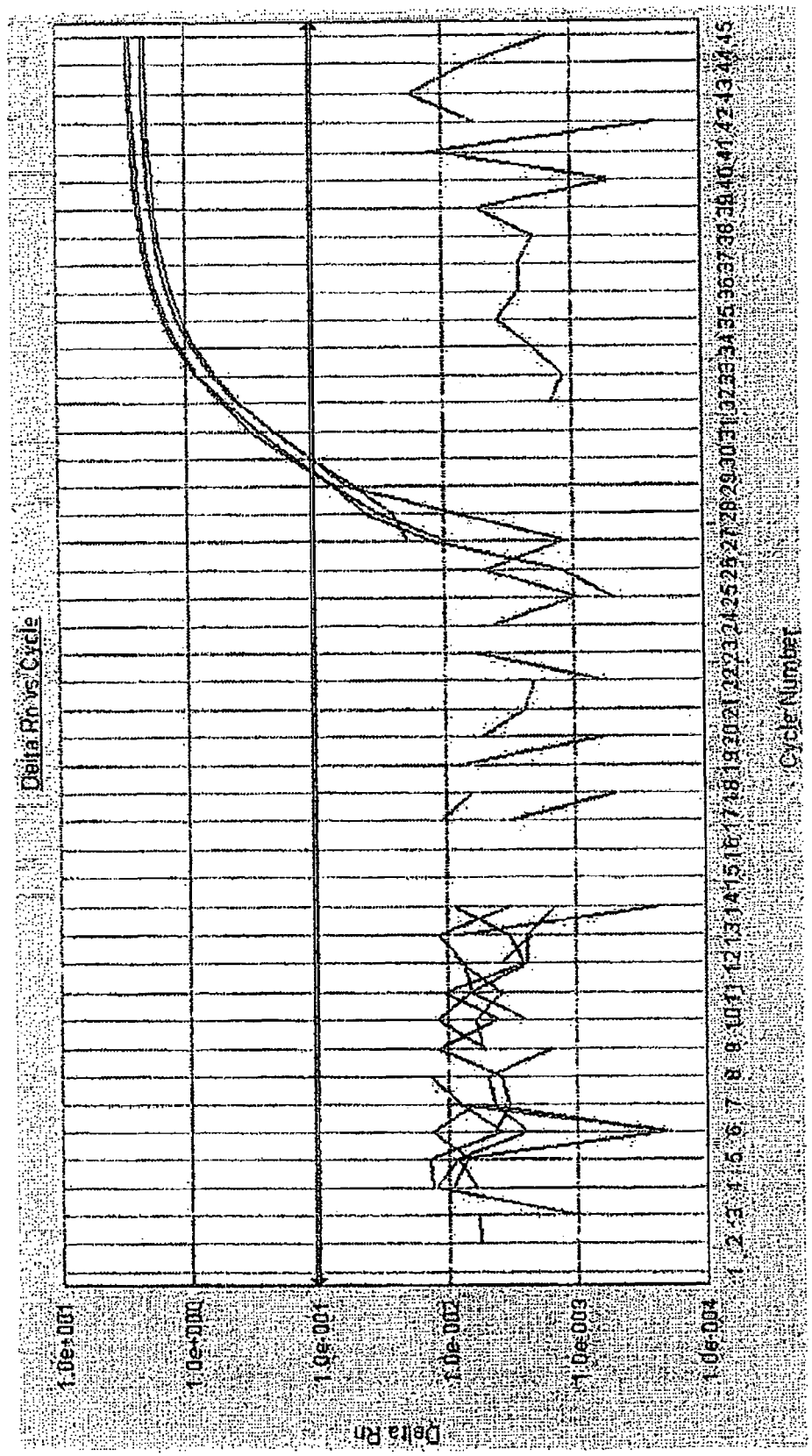

FIG. 2 is a graph for: A) DNA isolated from pure *Chlamydia trachomatis* (CT), B) *Chlamydia trachomatis* mixed with other bacteria, and C) mixed DNA that contains no *Chlamydia trachomatis* DNA, all done in duplicate. The x axis of the graph represents the number of cycles (cycle number) and the y axis represents the fluorescent intensity after the elimination of the background signal.

EXAMPLES

Example 1

Introduction

*Chlamydia trachomatis* is an obligate intracellular Gram-negative bacterium. Fifteen different serotypes of it are known at present, including eight (D-K) that cause urogenital infections. The infection is generally asymptomatic in women, and untreated infections can lead to endometritis, salpingitis and infertility. It is believed that screening for asymptomatic infections would reduce the transmission of CT and the development of serious complications[1] (raised numbers denote literature references listed later). Nucleic acid replication tests have now replaced antigen detection and cell culture for the diagnosis of infections by CT. A great number of commercial and in-house nucleic acid replication tests have been described. Most of the earlier replication tests[2-8] have major drawbacks, such as manual processing, open systems, separate steps for replication and Amplicon analysis, and sensitivity to contamination. It has been found that real-time PCR is a sensitive alternative that is easy to carry out. Despite improvements in real-time PCR, the type-specific inhibitory substances present in some clinical samples cannot always be reliably removed from the sample during preparation. This inhibition can be recognized by the use of an internal reference. Especially when samples that are not approved by the FDA, such as rectal smears, are to be tested for the presence of trachomatis, a type of sample that has received much attention with the recent outbreak of *Chlamydia trachomatis*-induced LGV amongst men who have sex with men (MSM). This study deals with the development and validation of real-time PCR with an internal reference that takes care both of inhibition and nucleic acid extraction from clinical samples.

Material and Methods

Development of Real-Time PCR

We have developed a real-time PCR (TaqMan assay) directed at the cryptic plasmid of trachomatis. The primers and the probe were developed with Primer Express 1.0 (from Opliet Biedsysteem). Real-time PCR reactions were carried out in a PCR volume of 30 µl, containing 1× TaqMan Mastermix (from Applied Biosystems), 300 nM of each primer, 150 nM of each probe, and 10 µl of the extracted DNA, apart from the samples that were prepared with the Roche Kit (14 µl). Replication and detection were carried out with an ABI Prism 7000 sequence detection system (from Applied Biosystems) under standard PCR conditions, stipulated by the manufacturer, using 45 cycles.

Determination of the Sensitivity

The sensitivity was determined by carrying out the real-time PCR on a previously described serial dilution of DNA from the LGV L2 strain of *Chlamydia trachomatis* (region 10-0.001 IFU). The results were compared with our previously reported in-house CT-PCR and a commercially available PCR(COBAS Amplicor from Roche).

Determination of the Specificity

The specificity was determined in silico, by carrying out a BLAST search for all the oligonucleotides used in this study. The specificity was further investigated by carrying out a CT-PCR on various bacterial species, namely *Staphylococcus aureus* (ATCC 25923), *Staphylococcus epidermidis* (ATCC 1228), *Klebsiella pneumoniae* (ATCC 13883), *Candida albicans* (ATCC 90028), *Protheus mirabilis* (ATCC 43071), *Pseudomonas aeruginosa* (ATCC 27853), *Enterococcus faecium* (clinical isolate), *Moraxella catarrhalis* (clinical isolate), *Haemophilus influenza* (clinical isolate), as well as a panel containing all the serotypes of *Chlamydia trachomatis*.

Evaluation of Real-Time PCR

Clinical samples (cervical smears) that had been positive (N=100) and negative (N=100) in the COBAS Roche PCR method were tested in the new real-time PCR after 1) the isolation of DNA from the original samples collected in 2 SP with the HPPTP Kit (from Roche), and 2) the commercially available COBAS CT DNA Preparation Kit (CDPK).

Validation of the Internal Reference

The internal reference used in this study was an inventive and particularly suitable reference sample that makes it possible to check the tests for good performance. It uses the same primer binding sites as the new real-time CT assay, but has an artificial sequence as the probe binding site for monitoring the DNA isolation, including the lysis of the samples. In other words, the internal reference is a target DNA sequence that can be observed by using the same primers as those which are used for observing the *Chlamydia* described here, but it can also be observed with a hybridization probe that is different from the one used for observing the *Chlamydia* described here. For example, since the DNA at which this different hybridization probe is directed is different from the one used for the detection of *Chlamydia*. The target of the internal reference was transferred into the genome of an *E. coli* (DH5α strain) with the aid of the suicide vector pBSL182. By spiking the altered *E. coli* DH5α strain in the clinical samples, the DNA isolation and the primer-specific inhibition is monitored in each PCR amplification. The exact amount of spiked *E. coli* DH5α was determined by using a serial dilution (0-20, 000 cfu). The spiking was carried out both on the COBAS negative and on the COBAS positive clinical cervical smears, prior to the isolation of DNA in order to determine the amount of the internal reference sample needed for a reliable recovery without a drop in the sensitivity of the *Chlamydia trachomatis* assay. DNA was isolated from all the samples as described above, either by HPPTP or by CDPK.

Internal Reference Spiking of Clinical Samples

The clinical samples mentioned above were spiked with the optimum quantity of IR in order to validate the internal reference, which is also used to check the sample preparation procedure.

Results

Sensitivity and Specificity of the New Real-Time PCR

The lower limit of detection was determined by using serial dilutions of a *Chlamydia trachomatis* LGV L2 strain and analysing the results by real-time PCR, as described before[6]. The sensitivity was found to be 0.01 IFU/PCR. This sensitivity is identical to that of the previously developed non-real-time PCR, while a sensitivity of 1 IFU was reported for the commercially available PCR of Roche and for LCr of Abbott. The assay was capable of detecting all the serotypes of *Chlamydia trachomatis* present in the panel. The specificity of the real-time CT assay was investigated by comparing the quantifications of pure *Chlamydia trachomatis* with that of DNA from *Chlamydia trachomatis* mixed with DNA isolated from nine other bacterial types. As shown in FIG. 2, the PCR did not show any cross-reaction with alien DNA.

Evaluation of Real-Time PCR with Clinical Samples

All the clinical samples that had been found to be either positive (N=100) or negative (N=100) in the COBAS Roche PCR were tested by the new real-time PCR method after the isolation of DNA either by HPPTP or by the CDPK procedure: all the samples gave the same results as the original COBAS method.

Validation of the Internal Reference

Prior to the preparation of the samples with the aid of the HPPTP kit or the CDPK procedure, ten clinical samples were spiked with various serial dilutions of the modified *E. coli* DH5α strain, which showed that the best amount of the internal reference sample was 200 cfu in the HPPTP procedure and 2000 cfu in the CDPK procedure. To determine whether the addition of IR results in the same sensitivity, the same serial dilutions were tested after the addition of 200 cfu of IR. As shown in FIG. 1, the assay was linear between 1000 and 0.01 IFU/PCR for the assay including the IR, which means that 0.01 IFU/PCR remained the lower limit of detection.

Validation of the Internal Reference in Clinical Samples

Samples that were negative for *Chlamydia trachomatis* and contained the internal reference sample were replicated, and the resulting $C_I$ values were averaged to find the analytical variation in the values for *Chlamydia* and for the inhibition cut-off. The inhibition cut-off value was set at $C_I$=40.1 for the HPPTP and 37.1 for the CDPK. The cervical smears were then tested for infection by *Chlamydia trachomatis*, using our assay including IR. If both the internal reference sample and the *Chlamydia* sample were negative, the sample was regarded as inhibited, so it was examined again (N=6). If the sample turned out to be negative again, it was considered impossible to interpret (N=3). The internal reference sample was not considered when the *Chlamydia* sample was found to be positive. Samples were regarded as negative if the *Chlamydia* was negative and the internal reference sample was positive. The originally positive and negative COBAS test results were confirmed.

Discussion

One of the characteristics that are important for the amplification of microorganisms in clinical samples is the monitoring and checking of the procedure with the aid of internal references. For a pathogen-specific real-time PCR assay, the ideal internal reference sample would have to be added to the clinical samples before the treatment, the recovery during the nuclein extraction and the replication either in a multiplex or in a competitive PCR with direct detection by fluorescent probes. None of the real-time PCR assays described so far[7-9] has such an internal reference capable of checking the sample preparation and the inhibition in the step in which *Chlamydia trachomatis* is detected. Most other real-time assays use other microorganisms for monitoring the extraction of DNA, an example being the herpesvirus PhHV[10]. Although this method can monitor the efficiency of the DNA preparation, it cannot monitor the primary location-specific inhibition, and since these assays are mostly based on duplex PCR, it can be assumed that competition between the two amplicons leads to a reduced sensitivity of the assays. The differences between the HPPTP with only 200 cfu of internal reference sample in comparison with the 2000 cfu for the CDPK procedure is most probably the result of the fact that the HPPTP assay leads to pure DNA, while the CDPK only gives a preparation that is clean enough for the assay. It is interesting that no difference was found in the diagnostic sensitivity between the two procedures, most probably because, in a *Chlamydia*-positive epithelial cell, a single *Chlamydia* inclusion can contain more than 10,000 *Chlamydia* particles, each having about 10 plasmid targets. The internal reference represented in this study can monitor simultaneously the DNA preparation efficiency and the primer-specific PCR inhibition in the same PCR assay. This fact, in combination with the rapid and easier Roche COBAS CT DNA preparation kit, makes for a very reliable, rapid and cost-effective real-time PCR *Chlamydia* assay that is highly suitable for routine work.

REFERENCES

1. S. A. Morre, R. Welte and M. J. Postma: "Major improvements in cost effectiveness of screening women for *Chlamydia trachomatis* using pooled urine specimens and high performance testing", *Sex. Transm. Infect.*, 78 (2002), pp. 74-75
2. N. DiDomenico, H. Link, R. Knobel, T. Caratsch, W. Weschler, Z. G. Loewy et al.: "COBAS AMPLICOR: fully automated RNA and DNA amplification and detection system for routine diagnostic PCR", *Clin. Chem.*, 42 (1996), pp. 1915-23
3. H. Keegan, A. Malkin, M. Griffin, F. Ryan and H. Lambkin: "Validation of a multiplex PCR assay for the simultaneous detection of human papillomavirus and *Chlamydia trachomatis* in cervical PreservCyt samples", *Clin. Chem.*, 51 (2005), pp. 1301-2
4. S. A. Morre, P. Sillekens, M. V. Jacobs, P. van Aarle, S. de Blok, B. van Gemen et al.: "RNA amplification by nucleic acid sequence-based amplification with an internal standard enables reliable detection of *Chlamydia trachomatis* in cervical scrapings and urine samples", *J. Clin. Microbiol.*, 34 (1996), pp. 3108-14
5. S. A. Morre, I. G. van Valkengoed, R. M. Moes, A. J. Boeke, C. J. Meijer and A. J. van den Brule: "Determination of *Chlamydia trachomatis* prevalence in an asymptomatic screening population: performances of the LCx and COBAS Amplicor tests with urine specimens", *J. Clin. Microbiol.*, 37 (1999), pp. 3092-6
6. R. Roosendaal, J. M. Walboomers, O. R. Veltman, I. Melgers, C. Burger, O. P. Bleker et al.: "Comparison of different primer sets for detection of *Chlamydia trachomatis* by the polymerase chain reaction", *J. Med. Microbiol.*, 38 (1993), pp. 426-433
7. M. Eickhoff, T. Laue, T. Ruckes, S. O. Cramer, G. Krupp and C. Tiemann: "Ultra-rapid detection of *Chlamydia trachomatis* by real-time PCR in the LightCycler using SYBR green technology or 5'-nuclease probes", *Clin. Lab.*, 49 (2003), pp. 217-225
8. H. Jalal, H. Stephen, M. D. Curran, J. Burton, M. Bradley and C. Came: "Development and validation of a rotor-gene real-time PCR assay for detection, identification and quantification of *Chlamydia trachomatis* in a single reaction", *J. Clin. Microbiol.*, 44 (2006), pp. 206-213
9. M. G. Koenig, S. L. Kosha, B. L. Doty and D. G. Heath: "Direct comparison of the BD ProbeTec ET system with in-house LightCycler PCR assays for detection of *Chlamydia trachomatis* and *Neisseria gonorrhoeae* from clinical specimens", *J. Clin. Microbiol.*, 42 (2004), pp. 5751-6
10. G. J. van Doornum, J. Guldemeester, A. D. Osterhaus and H. G. Niesters: "Diagnosing herpesvirus infections by real-time amplification and rapid culture", J. Clin. Microbiol., 41 (2003), pp. 576-580

Example 2

As described above, it was found that problems occur with the observation of *Chlamydia trachomatis* under certain conditions. An article by Söderblom et al. (*Euro Surveill.* 2006 Dec. 7; 11 (12)): E061207.1) entitled "Impact of a genetic variant of *Chlamydia trachomatis* on national detection rates in Sweden" reports that part of the sexually transmitted *Chlamydia trachomatis* infections could not be observed in Sweden by standard laboratory tests produced by Abbott and Roche, and that *Chlamydia* bacteria with a variation in the genetic region at which the primers had been directed were not observed. Tests carried out by the method used in Example 1 have shown that such *Chlamydia trachomatis* types can indeed be observed by using primer pairs according to the present invention.

The invention claimed is:

1. A primer pair to amplify *Chlamydia trachomatis* DNA, wherein a first isolated primer binds to the region corresponding to the nucleotide numbers from 4291 to 4320 of SEQ ID NO:1, and a second isolated primer binds to the region corresponding to the nucleotide numbers from 4351 to 4391 of SEQ ID NO:1, wherein (i) the sequence in between the first and second primer binding region corresponding to SEQ ID NO:1 can be amplified and (ii) the length of the first and second primer is 15-40 nucleotides.

2. The primer pair of claim 1, wherein the first primer binds to the region corresponding to the nucleotide numbers from 4296 to 4318 of SEQ ID NO:1, and the second primer binds to the region corresponding to the nucleotide numbers from 4361 to 4382 of SEQ ID NO:1.

3. The primer pair of claim 1, wherein the first primer binds to the nucleotide sequence, GGATTGACTCCGACAACG-TATTC (SEQ ID NO: 2), or the complementary form thereof, and the second primer binds to the nucleotide sequence, TGCCCTTTCTAATGGCAATGAT (SEQ ID NO: 3), or the complementary form thereof.

4. The primer pair of claim 1, wherein the first and second primer comprises the nucleotide sequence, 5'-GGAT-TGACTCCGACAACGTATTC-3' (SEQ ID NO: 5), or the complementary form thereof, and the second primer comprises the nucleotide sequence, 5'-ATCATTGCC ATTA-GAAAGGGCA-3' (SEQ ID NO: 6), or the complementary form thereof.

5. The primer pair of claim 1, further comprising an additional isolated primer, wherein the additional primer differs in sequence from the first or the second primer in one nucleotide.

6. The primer pair and additional isolated primer of claim 5, wherein the additional isolated primer comprises the nucleotide sequence, 5'-GGATTGACTCCAACAACGTATTC-3' (SEQ ID NO:7), or the complementary form thereof.

7. The primer pair of claim 1, wherein the first isolated primer and the second isolated primer are separate.

8. The primer pair of claim 1, wherein the first primer and the second primer are mixed.

9. A method to detect *Chlamydia trachomatis*, the method comprising
  (a) performing DNA amplification using DNA that is derived from a sample and a primer pair to amplify *Chlamydia trachomatis* DNA; and
  (b) detecting an amplification product,
wherein the primer pair to amplify *Chlamydia trachomatis* DNA comprises a first primer which binds to the region corresponding to the nucleotide numbers from 4291 to 4320 of SEQ ID NO:1, and a second primer which binds to the region corresponding to the nucleotide numbers from 4351 to 4391 of SEQ ID NO:1, wherein (i) the sequence in between the first and second primer binding region corresponding to SEQ ID NO:1 can be amplified and (ii) the length of the first and second primer is 15-40 nucleotides.

10. The method of claim 9, wherein the first primer binds to the region corresponding to the nucleotide numbers from 4291 to 4320 of SEQ ID NO:1, and the second primer binds to the region corresponding to the nucleotide numbers from 4355 to 4385 of SEQ ID NO:1.

11. The method of claim 9, wherein the first primer binds to the region corresponding to the nucleotide numbers from 4296 to 4318 of SEQ ID NO:1, and the second primer binds to the region corresponding to the nucleotide numbers from 4361 to 4382 of SEQ ID NO:1.

12. The method of claim 9, wherein the first primer binds to the nucleotide sequence, GGATTGACTCCGACAACG-TATTC (SEQ ID NO: 2), or the complementary form thereof, and the second primer binds to the nucleotide sequence, TGCCCTTTCTAATGGCAATGAT (SEQ ID NO: 3), or the complementary form thereof.

13. A kit for detecting *Chlamydia trachomatis* by carrying out PCR using DNA obtained from a sample, wherein the kit comprises a primer pair to amplify *Chlamydia trachomatis* DNA, wherein a first isolated primer binds to the region corresponding to the nucleotide numbers from 4291 to 4320 of SEQ ID NO:1, and a second isolated primer which binds to the region corresponding to the nucleotide numbers from 4351 to 4391 of SEQ ID NO:1, wherein (i) the sequence in between the first and second primer binding region corresponding to SEQ ID NO:1 can be amplified and (ii) the length of the first and second primer is 15-40 nucleotides.

14. The kit of claim 13, wherein the first primer binds to the region corresponding to the nucleotide numbers from 4291 to 4320 of SEQ ID NO:1, and the second primer binds to the region corresponding to the nucleotide numbers from 4355 to 4385 of SEQ ID NO:1.

15. The kit of claim 13, wherein the first primer binds to the region corresponding to the nucleotide numbers from 4296 to 4318 of SEQ ID NO:1, and the second primer binds to the region corresponding to the nucleotide numbers from 4361 to 4382 of SEQ ID NO:1.

16. The kit of claim 13, wherein the first primer binds to the nucleotide sequence, GGATTGACTCCGACAACGTATTC (SEQ ID NO: 2), or the complementary form thereof, and the second primer binds to the nucleotide sequence, TGC-CCTTTCTAATGGCAATGAT (SEQ ID NO: 3), or the complementary form thereof.

17. The kit of claim 13, wherein the first isolated primer and the second isolated primer are separate.

18. The kit of claim 13, wherein the first primer and the second primer are mixed.

* * * * *

SEQUENCE LISTING

<160> NUMBER OF SEQ ID NOS: 8

<210> SEQ ID NO 1
<211> LENGTH: 7499
<212> TYPE: DNA

<213> ORGANISM: Chlamydia trachomatis

<400> SEQUENCE: 1

```
ggtaagtcct ctagtacaaa cacccccaat attgtgatat aattaaaatt atattcatat     60
tctgttgcca gaaaaaacac ttttaggcta tattagagcc atcttctttg aagcgttgtc    120
ttctcgagaa gatttatcgt acgcaaatat catctttgcg gttgcgtgtc ctgtgacctt    180
cattatgtcg gagtctgagc accctaggcg tttgtactcc gtcacagcgg ttgctcgaag    240
cacgtgcggg gttatcttaa aagggattgc agcttgtagt cctgcttgag agaacgtgcg    300
ggcgatttgc cttaacccca ccatttttcc ggagcgagtt acgaagacaa aacctcttcg    360
ttgaccgatg tactcttgta gaaagtgcat aaacttctga ggataagtta taataatcct    420
cttttctgtc tgacggttct taagctggga gaaagaaatg gtagcttgtt ggaaacaaat    480
ctgactaatc tccaagctta agacttcaga ggagcgttta cctccttgga gcattgtctg    540
ggcgatcaac caatcccggg cattgatttt ttttagctct tttaggaagg acgctgtttg    600
caaactgttc atcgcatctg tttttactat ttccctggtt ttaaaaaatg ttcgactatt    660
ttcttgttta gaaggttgcg ctatagcgac tattccttga gtcatcctgt ttaggaatct    720
tgttaaggaa atatagcttg ctgctcgaac ttgtttagta ccttcggtcc aagaagtctt    780
ggcagaggaa actttttttaa tcgcatctag aattagatta tgatttaaaa gggaaaactc    840
ttgcagattc atatccaagg acaatagacc aatcttttct aaagacaaaa aagatcctcg    900
atatgatcta caagtatgtt tgttgagtga tgcggtccaa tgcataataa cttcgaataa    960
ggagaagctt ttcatgcgtt tccaatagga ttcttggcga atttttaaaa cttcctgata   1020
agacttttcg ctatattcta acgacatttc ttgctgcaaa gataaaatcc ctttacccat   1080
gaaatccctc gtgatataac ctatccgtaa aatgtcctga ttagtgaaat aatcaggttg   1140
ttaacaggat agcacgctcg gtattttttt atataaacat gaaaactcgt tccgaaatag   1200
aaaatcgcat gcaagatatc gagtatgcgt tgttaggtaa agctctgata tttgaagact   1260
ctactgagta tattctgagg cagcttgcta attatgagtt taagtgttct catcataaaa   1320
acatattcat agtatttaaa tacttaaaag acaatggatt acctataact gtagactcgg   1380
cttgggaaga gcttttgcgg cgtcgtatca aagatatgga caaatcgtat ctcgggttaa   1440
tgttgcatga tgctttatca aatgacaagc ttagatccgt ttctcatacg gttttcctcg   1500
atgatttgag cgtgtgtagc gctgaagaaa atttgagtaa tttcattttc cgctcgttta   1560
atgagtacaa tgaaaatcca ttgcgtagat ctccgtttct attgcttgag cgtataaagg   1620
gaaggcttga cagtgctata gcaaagactt tttctattcg cagcgctaga ggccggtcta   1680
tttatgatat attctcacag tcagaaattg gagtgctggc tcgtataaaa aaaagacgag   1740
caacgttctc tgagaatcaa aattctttct ttgatgcctt cccaacagga tacaaggata   1800
ttgatgataa aggagttatc ttagctaaag gtaatttcgt gattatagca gctaggccat   1860
ctatagggaa aactgcttta gctatagaca tggcgataaa tcttgcggtt actcaacagc   1920
gtagagttgg tttcctatct ctagaaatga gcgcaggtca aattgttgag cggattattg   1980
ctaatttaac aggaatatct ggtgaaaaat tacaaagagg ggatctctct aaagaagaat   2040
tattccgagt agaagaagct ggagaaacag ttagagaatc acatttttat atctgcagtg   2100
atagtcagta taagcttaat ttaatcgcga atcagatccg gttgctgaga aaagaagatc   2160
gagtagacgt aatatttatc gattacttgc agttgatcaa ctcatcggtt ggagaaaatc   2220
gtcaaaatga aatagcagat atatctagaa ccttaagagg tttagcctca gagctaaaca   2280
```

```
ttcctatagt tgtttatcc caactatcta gaaaagttga ggatagagca aataaagttc    2340
ccatgctttc agatttgcga gacagcggtc aaatagagca agacgcagat gtgattttgt    2400
ttatcaatag gaaggaatcg tcttctaatt gtgagataac tgttgggaaa aatagacatg    2460
gatcggtttt ctcttcggta ttacatttcg atccaaaaat tagtaaattc tccgctatta    2520 aaaagtatg gtaaattata gtaactgcca cttcatcaaa agtcctatcc accttgaaaa     2580
tcagaagttt ggaagaagac ctggtcaatc tattaagata tctcccaaat tggctcaaaa    2640
tgggatggta gaagttatag gtcttgatt tctttcatct cattaccatg cattagcagc     2700
tatccaaaga ttgctgactg caacgaatta caaggggaac acaaaagggg ttgttttatc    2760
cagagaatca aatagttttc aatttgaagg atggatacca agaatccgtt ttacaaaaac    2820
tgaattctta gaggcttatg gagttaagcg gtataaaaca tccagaaata agtatgagtt    2880
tagtggaaaa gaagctgaaa ctgctttaga agccttatac catttaggac atcaaccgtt    2940
tttaatagtg gcaactagaa ctcgatggac taatggaaca caaatagtag accgttacca    3000
aactctttct ccgatcatta ggatttacga aggatgggaa ggtttaactg acgaagaaaa    3060
tatagatata gacttaacac cttttaattc accatctaca cggaaacata aagggttcgt    3120
tgtagagcca tgtcctatct tggtagatca aatagaatcc tactttgtaa tcaagcctgc    3180
aaatgtatac caagaaataa aaatgcgctt cccaaatgca tcaaagtatg cttacacatt    3240
tatcgactgg gtgattacag cagctgcgaa aaagagacga aaattaacta aggataattc    3300
ttggccagaa aacttgttct taaacgttaa cgttaaaagt cttgcatata ttttaaggat    3360
gaatcggtac atttgtacaa ggaactggaa aaaaatcgag ttagctatcg ataaatgtat    3420
agaaatcgcc attcagcttg gttggttatc tagaagaaaa cgcattgaat ttctggattc    3480
ttctaaactc tctaaaaaag aaattctata tctaaataaa gagcgttttg aagaaataac    3540
taagaaatct aaagaacaaa tggaacaatt agaacaagaa tctattaatt aatagcaaac    3600
ttgaaactaa aaacctaatt tatttaaagc tcaaataaaa aaagagttt aaaatgggaa     3660 attctggttt ttatttgtat aacactcaaa actgcgtctt tgctgataat atcaaagttg    3720
ggcaaatgac agagccgctc aaggaccagc aaataatcct tgggacaaca tcaacacctg    3780
tcgcagccaa aatgacagct tctgatggaa tatctttaac agtctccaat aatccatcaa    3840
ccaatgcttc tattacaatt ggtttggatg cggaaaaagc ttaccagctt attctagaaa    3900
agttgggaga tcaaattctt ggtggaattg ctgatactat tgttgatagt acagtccaag    3960
atattttaga caaaatcaca acagacccct ctctaggttt gttgaaagct tttaacaact    4020
ttccaatcac taataaaatt caatgcaacg ggttattcac tcccaggaac attgaaactt    4080
tattaggagg aactgaaata ggaaaattca cagtcacacc caaaagctct gggagcatgt    4140
tcttagtctc agcagatatt attgcatcaa gaatggaagg cggcgttgtt ctagctttgg    4200
tacgagaagg tgattctaag ccctacgcga ttagttatgg atactcatca ggcgttccta    4260
atttatgtag tctaagaacc agaattatta atacaggatt gactccgaca acgtattcat    4320
tacgtgtagg cggtttagaa agcggtgtgg tatgggttaa tgccctttct aatggcaatg    4380
atattttagg aataacaaat acttctaatg tatcttttt ggaggtaata cctcaaacaa     4440
acgcttaaac aattttttatt ggatttttct tataggtttt atatttagag aaaaaagttc    4500
gaattacggg gtttgttatg caaaataaaa gcaaagtgag ggacgatttt attaaaattg    4560
ttaaagatgt gaaaaagat tccccgaat tagacctaaa aatacgagta aacaaggaaa      4620
aagtaacttt cttaaattct cccttagaac tctaccataa aagtgtctca ctaattctag    4680
```

```
gactgcttca acaaatagaa aactctttag gattattccc agactctcct gttcttgaaa    4740
aattagagga taacagttta aagctaaaaa aggctttgat tatgcttatc ttgtctagaa    4800
aagacatgtt ttccaaggct gaatagataa cttactctaa cgttggagtt gatttgcaca    4860
ccttagtttt ttgctctttt aagggaggaa ctggaaaaac aacactttct ctaaacgtgg    4920
gatgcaactt ggcccaattt ttagggaaaa aagtgttact tgctgaccta gacccgcaat    4980
ccaatttatc ttctggattg ggggctagtg tcagaagtaa ccaaaaaggc ttacacgaca    5040
tagtatacac atcaaacgat ttaaaatcaa tcatttgcga aacaaaaaaa gatagtgtgg    5100
acctaattcc tgcatcattt ttatccgaac agtttagaga attggatatt catagaggac    5160
ctagtaacaa cttaaagtta tttctgaatg agtactgcgc tccttttat gacatctgca     5220 taatagacac tccacctagc ctaggagggt aacgaaaga agcttttgtt gcaggagaca     5280
aattaattgc ttgtttaact ccagaacctt tttctattct agggttacaa aagatacgtg    5340
aattcttaag ttcggtcgga aaacctgaag aagaacacat tcttggaata gctttgtctt    5400
tttgggatga tcgtaactcg actaaccaaa tgtatataga cattatcgag tctatttaca    5460
aaaacaagct ttttcaaca aaaattcgtc gagatatttc tctcagccgt tctcttctta     5520
aagaagattc tgtagctaat gtctatccaa attctagggc cgcagaagat attctgaagt    5580
taacgcatga aatagcaaat attttgcata tcgaatatga acgagattac tctcagagga    5640
caacgtgaac aaactaaaaa aagaagcgaa tgtcttttt aaaaaaaatc aaactgccgc     5700
ttctttagat tttaagaaga cgcttccttc cattgaacta ttctcagcaa ctttgaattc    5760
tgaggaaagt cagagtttgg atcaattatt tttatcagag tcccaaaact attcggatga    5820 agaatttat caagaagaca tcctagcggt aaaactgctt actggtcaga taaaatccat      5880
acagaagcaa cacgtacttc ttttaggaga aaaaatctat aatgctagaa aaatcctgag    5940
taaggatcac ttctcctcaa caactttttc atcttggata gagttagttt ttagaactaa    6000
gtcttctgct tacaatgctc ttgcatatta cgagcttttt ataaacctcc ccaaccaaac    6060
tctacaaaaa gagtttcaat cgatccccta taaatccgca tatattttgg ccgctagaaa    6120
aggcgattta aaaaccaagg tcgatgtgat agggaaagta tgtggaatgt cgaactcatc    6180
ggcgataagg gtgttggatc aatttcttcc ttcatctaga acaaagacg ttagagaaac     6240 gatagataag tctgattcag agaagaatcg ccaattatct gatttcttaa tagagatact    6300
tcgcatcatg tgttccggag tttctttgtc ctcctataac gaaaatcttc tacaacagct    6360
ttttgaactt tttaagcaaa agagctgatc ctccgtcagc tcatatatat atctattata    6420
tatatatatt tagggatttg attttacgag agagatttgc aactcttggt ggtagacttt    6480
gcaactcttg gtggtagact ttgcaactct tggtggtaga cttttgcaact cttggtggta    6540 gacttggtca taatggactt ttgttgaaaa atttcttaaa atcttagagc tccgattttg    6600
aatagctttg gttaagaaaa tgggctcgat ggctttccat aaaagtaggt tgttcttaac    6660
ttttggggac gcgtcggaaa tttggttatc tactttatct catctaacta gaaaaaatta    6720
tgcgtctggg attaactttc ttgtttcttt agagattctg gatttatcgg aaaccttgat    6780
aaaggctatt tctcttgacc acagcgaatc tttgtttaaa atcaagtctc tagatgtttt    6840
taatggaaaa gtcgtttcag aggcctctaa acaggctaga gcggcatgct acatatcttt    6900
cacaaagttt ttgtatagat tgaccaaggg atatattaaa cccgctattc cattgaaaga    6960
ttttggaaac actacatttt ttaaaatccg agacaaaatc aaaacagaat cgatttctaa    7020
gcaggaatgg acagtttttt ttgaagcgct ccggatagtg aattatagag actatttaat    7080
```

-continued

```
cggtaaattg attgtacaag ggatccgtaa gttagacgaa attttgtctt tgcgcacaga    7140
cgatctattt tttgcatcca atcagatttc ctttcgcatt aaaaaaagac agaataaaga    7200
aaccaaaatt ctaatcacat ttcctatcag cttaatggag gagttgcaaa aatacacttg    7260
tgggagaaat gggagagtat ttgtttctaa aatagggatt cctgtaacaa caagtcaggt    7320
tgcgcataat tttaggcttg cagagttcta tagtgctatg aaaaaaaaat tactcctaga    7380
gtacttcgtg caagcgcttt gattcattta aagcaaatag gattaaaaga tgaggaaatc    7440
atgcgtattt cctgtctttc atcgagacaa agtgtgtgtt cttattgttc tggggaaga     7499
```

<210> SEQ ID NO 2
<211> LENGTH: 23
<212> TYPE: DNA
<213> ORGANISM: Chlamydia trachomatis

<400> SEQUENCE: 2
ggattgactc cgacaacgta ttc                                              23

<210> SEQ ID NO 3
<211> LENGTH: 22
<212> TYPE: DNA
<213> ORGANISM: Chlamydia trachomatis

<400> SEQUENCE: 3 tgcccttct aatggcaatg at                                                22

<210> SEQ ID NO 4
<211> LENGTH: 28
<212> TYPE: DNA
<213> ORGANISM: Chlamydia trachomatis

<400> SEQUENCE: 4
tacgtgtagg cggtttagaa agcggtgt                                         28

<210> SEQ ID NO 5
<211> LENGTH: 23
<212> TYPE: DNA
<213> ORGANISM: Chlamydia trachomatis

<400> SEQUENCE: 5
ggattgactc cgacaacgta ttc                                              23

<210> SEQ ID NO 6
<211> LENGTH: 22
<212> TYPE: DNA
<213> ORGANISM: Chlamydia trachomatis

<400> SEQUENCE: 6
atcattgcca ttagaaaggg ca                                               22

<210> SEQ ID NO 7
<211> LENGTH: 23
<212> TYPE: DNA
<213> ORGANISM: Chlamydia trachomatis

<400> SEQUENCE: 7
ggattgactc caacaacgta ttc                                              23

```
<210> SEQ ID NO 8
<211> LENGTH: 29
<212> TYPE: DNA
<213> ORGANISM: Chlamydia trachomatis

<400> SEQUENCE: 8
acaccgcttt ctaaaccgcc tacacgtaa                                          29
```